(12) United States Patent
Khan

(10) Patent No.: US 7,392,093 B2
(45) Date of Patent: Jun. 24, 2008

(54) ELECTRICAL STIMULATION SYSTEM INCLUDING A DEVICE FOR PARTIALLY SHIELDING ELECTRICAL ENERGY EMITTED FROM ONE OR MORE ELECTRICAL STIMULATION LEADS IMPLANTED IN A HUMAN'S BODY

(75) Inventor: Yasin N Khan, Allentown, PA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 567 days.

(21) Appl. No.: 10/950,116

(22) Filed: Sep. 24, 2004

(65) Prior Publication Data

US 2005/0137668 A1   Jun. 23, 2005

Related U.S. Application Data

(60) Provisional application No. 60/506,289, filed on Sep. 26, 2003.

(51) Int. Cl.
*A61N 1/05* (2006.01)
(52) U.S. Cl. .......................................... 607/118; 600/377
(58) Field of Classification Search .................. 607/118; 128/899; 600/377
See application file for complete search history.

(56) References Cited

U.S. PATENT DOCUMENTS

| 4,341,221 | A | * | 7/1982 | Testerman | .................. 600/377 |
| 4,628,942 | A | | 12/1986 | Sweeney et al. | ............. 128/784 |
| 5,282,468 | A | * | 2/1994 | Klepinski | .................... 600/377 |
| 5,643,330 | A | | 7/1997 | Holsheimer et al. | ........... 607/46 |
| 5,755,750 | A | * | 5/1998 | Petruska et al. | ............... 607/75 |
| 5,899,922 | A | | 5/1999 | Loos | .............................. 607/2 |
| 6,205,361 | B1 | | 3/2001 | Kuzma et al. | |
| 6,505,078 | B1 | | 1/2003 | King et al. | ..................... 607/67 |
| 6,522,932 | B1 | | 2/2003 | Kuzma et al. | |
| 6,587,733 | B1 | | 7/2003 | Cross, Jr. et al. | |
| 6,907,295 | B2 | * | 6/2005 | Gross et al. | .................. 607/118 |
| 6,909,918 | B2 | | 6/2005 | Stypulkowski | |
| 2003/0028147 | A1 | * | 2/2003 | Aves et al. | ............. 604/164.06 |
| 2005/0033393 | A1 | * | 2/2005 | Daglow | ...................... 607/116 |

OTHER PUBLICATIONS

PCT, Notification of Transmittal of the International Search Report and the Written Opinion of the International Searching Authority, or the Declaration, PCT/US2004/031320, 14 pages, Jan. 11, 2005.

\* cited by examiner

*Primary Examiner*—Carl H. Layno
*Assistant Examiner*—Yun Haeng Lee
(74) *Attorney, Agent, or Firm*—Christopher S. L. Crawford; Peter Lando; Melissa Acosta

(57) ABSTRACT

In one embodiment, a device is provided for partially shielding electrical energy emitted from an electrical stimulation lead implanted in a human's body to enable stimulation of the human's nerve tissue, the lead including one or more electrodes operable to stimulate the nerve tissue. The device includes an anterior concave surface adapted to contact and at least partially surround a posterior side of the lead such that the lead is positioned between the anterior concave surface and the nerve tissue when the device and the lead are implanted in the body. The device includes a posterior convex surface coupled to the anterior concave surface and adapted to contact the body tissue opposite the nerve tissue. The device is adapted to partially shield electrical energy emitted from one or more electrodes on a posterior side of the lead when the device and the lead are implanted in the body to reduce a quantity of electrical energy reaching the body tissue opposite the nerve tissue.

6 Claims, 5 Drawing Sheets

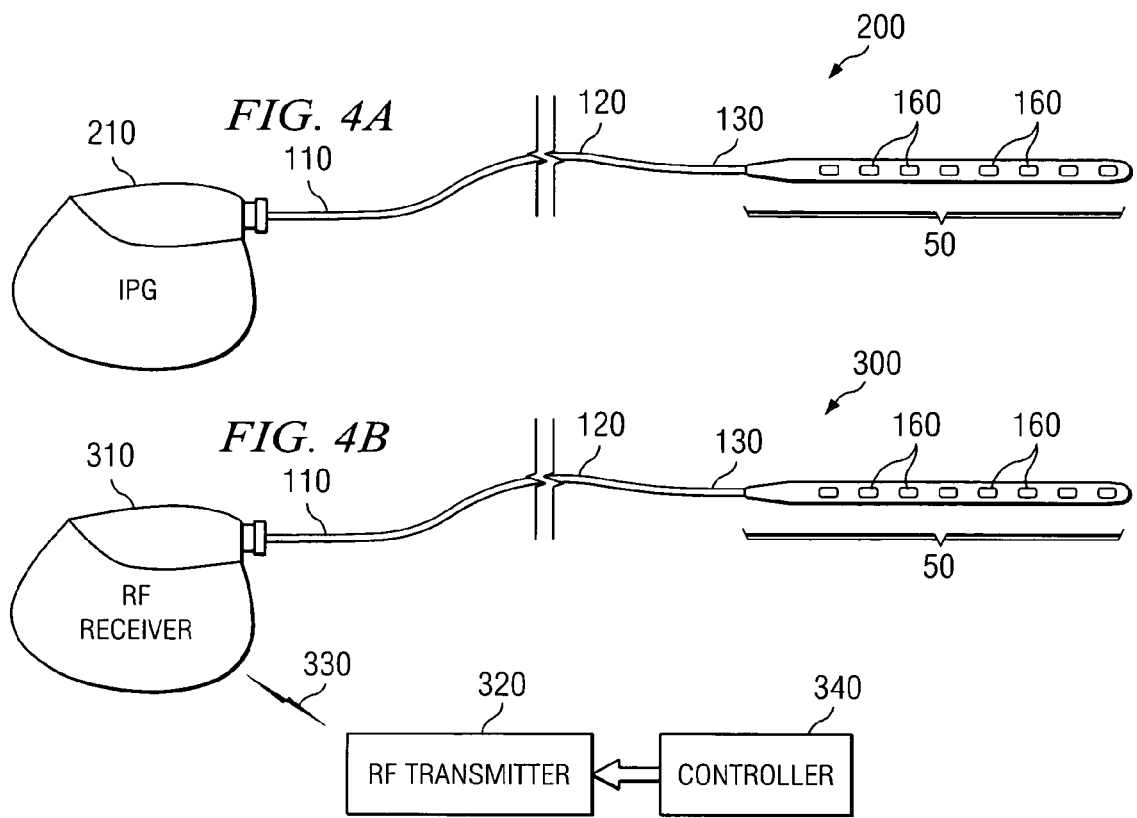
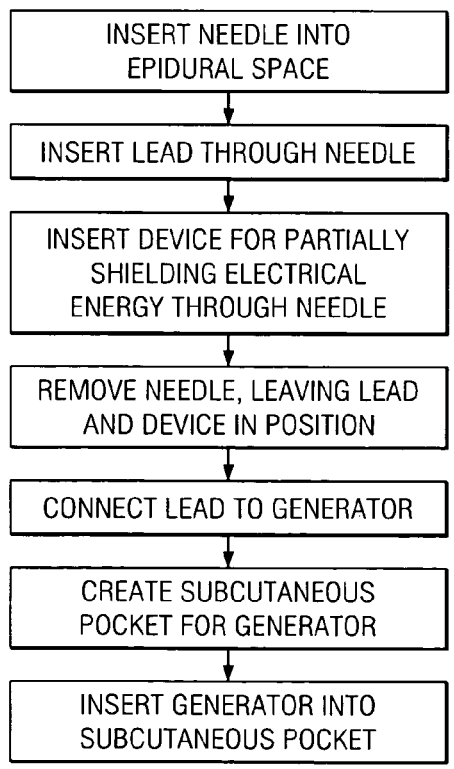

ELECTRICAL STIMULATION SYSTEM INCLUDING A DEVICE FOR PARTIALLY SHIELDING ELECTRICAL ENERGY EMITTED FROM ONE OR MORE ELECTRICAL STIMULATION LEADS IMPLANTED IN A HUMAN'S BODY

RELATED APPLICATIONS

This application claims the benefit under 35 U.S.C. § 119(e) of U.S. Provisional Application Ser. No. 60/506,289, filed Sep. 26, 2003.

TECHNICAL FIELD OF THE INVENTION

This invention relates generally to electrical stimulation systems designed for implantation into a human's body and more particularly to an electrical stimulation system including a device for partially shielding electrical energy emitted from one or more electrical stimulation leads implanted in a human's body.

BACKGROUND

Electrical energy is applied to the spinal cord and peripheral nerves to treat regions of the body that are affected by chronic pain from a variety of etiologies. One method of delivering electrical energy is to implant an electrode and position it in a precise location adjacent the spinal cord such that stimulation of the electrode causes a subjective sensation of numbness or tingling in the affected region of the body, known as "paresthesia." Pain managing electrical energy is commonly delivered through electrodes positioned external to the dura layer surrounding the spinal cord. The electrodes may be carried by either of two primary vehicles: a percutaneous lead and a laminotomy or "paddle" lead.

Percutaneous leads commonly have three or more electrodes. They are positioned above the dura layer using a needle that is passed through the skin, between the desired vertebrae and onto the top of the dura. Percutaneous leads deliver energy radially in all directions because of the circumferential nature of the electrode. Percutaneous leads can be implanted using a minimally invasive technique. In a typical percutaneous lead placement, a trial stimulation procedure is performed to determine the optimal location for the lead. Here, a needle is placed through the skin and between the desired vertebrae. The percutaneous lead is then threaded through the needle into the desired location over the spinal cord dura. Percutaneous leads may also be positioned in other regions of the body near peripheral nerves for the same purpose.

Laminotomy or paddle leads have a paddle-like configuration and typically possess multiple electrodes arranged in one or more independent columns. Paddle leads provide a more focused energy delivery than percutaneous leads because electrodes may be present on only one surface of the lead. Paddle leads may be desirable in certain situations because they provide more direct stimulation to a specific surface and require less energy to produce a desired effect. Because paddle leads are larger than percutaneous leads, they have historically required surgical implantation through a procedure known as partial laminectomy that requires the resection and removal of vertebral tissue.

SUMMARY OF THE INVENTION

In one embodiment, a device is provided for partially shielding electrical energy emitted from an electrical stimulation lead implanted in a human's body to enable stimulation of the human's nerve tissue. The electrical stimulation lead includes one or more electrodes operable to stimulate the human's nerve tissue. The device includes an anterior concave surface adapted to contact and at least partially surround a posterior side of the electrical stimulation lead such that the electrical stimulation lead is positioned between the anterior concave surface of the device and the human's nerve tissue when the device and the electrical stimulation lead are implanted in the human's body. The device includes a posterior convex surface coupled to the anterior concave surface and adapted to contact the human's body tissue opposite the human's nerve tissue. The device is adapted to partially shield electrical energy emitted from one or more electrodes on a posterior side of the electrical stimulation lead when the device and the electrical stimulation lead are implanted in the human's body to reduce the quantity of electrical energy reaching the human's body tissue opposite the human's nerve tissue.

BRIEF DESCRIPTION OF THE DRAWINGS

For a more complete understanding of the present invention and advantages thereof, reference is now made to the following description taken in conjunction with the accompanying drawings, in which:

FIG. 4A illustrates an example electrical stimulation system including an implantable pulse generator;

FIG. 4B illustrates an example electrical stimulation system including a wireless receiver; and FIGS. 5A-5B illustrate example steps for implanting an example electrical stimulation system into a human for electrical stimulation of the human's spinal nerve tissue.

DESCRIPTION OF EXAMPLE EMBODIMENTS

Figure 1A:
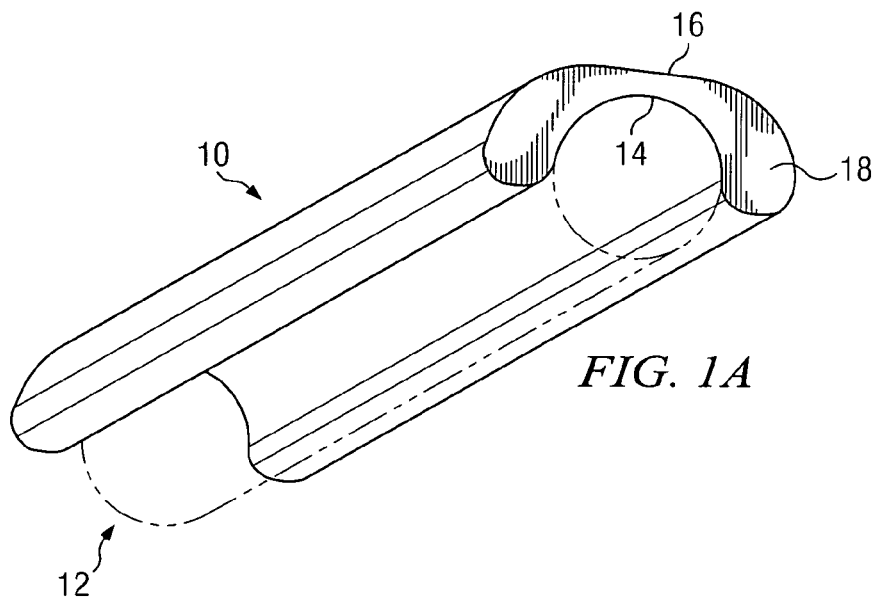
FIG. 1A illustrates a perspective view of an example device for partially shielding electrical energy emitted from an electrical stimulation lead implanted in a human's body, the device positioned proximate the electrical stimulation lead.
Figure 1B:
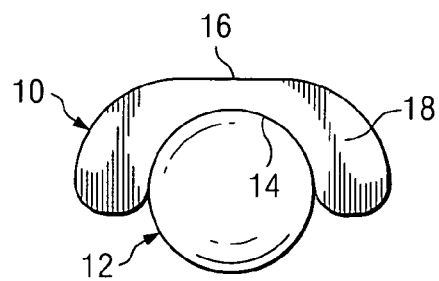
FIG. 1B illustrates a cross-sectional view of an example device for partially shielding electrical energy emitted from an electrical stimulation lead implanted in a human's body, the device positioned proximate the electrical stimulation lead.
Figure 1C:
FIG. 1C illustrates a side view of an example device for partially shielding electrical energy emitted from an electrical stimulation lead implanted in a human's body, the device positioned proximate the electrical stimulation lead.

FIGS. 1A-1C illustrate perspective, cross-sectional, and side views of an example device 10 for partially shielding electrical energy emitted from an electrical stimulation lead 12. For example, device 10 may be used to shield such electrical energy in a human who receives electrical stimulation treatment directed to the human's spinal nerve tissue, peripheral nerve tissue, or any other suitable target nerve tissue for pain management or other therapeutic purposes. Device 10 allows electrical stimulation of the target nerve tissue to occur while reducing the impact, if any, of such electrical stimulation on neighboring tissues. For example, where the target nerve tissue includes spinal nerve tissue such that electrical stimulation lead 12 and associated device 10 are implanted in the human's epidural space, device 10 may prevent at least some electrical energy from reaching the human's body tissue opposite the target nerve tissue such as the human's ligamentum flavum and associated tissue. Although device 10 may be used to partially shield electrical energy emitted from any type of electrical stimulation lead 12, device 10 may be particularly useful as a shield with respect to a percutaneous electrical stimulation lead 12 having circumferential electrodes that emit electrical energy radially in all directions.

In one embodiment, device 10 includes an anterior concave surface 14 coupled to a posterior convex surface 16. As used herein, the term "anterior" refers to the direction of the target nerve tissue to be stimulated and the term "posterior" refers to the direction of the body tissue opposite the target nerve tissue, regardless of true orientation within a human's body. For example, for electrical stimulation of spinal nerve tissue, anterior concave surface 14 of device 10 may face in a truly anterior direction with respect to the human's body, while for electrical stimulation of certain peripheral nerve tissue it may not. Anterior concave surface 14 is adapted to contact and at least partially surround a posterior side of electrical stimulation lead 12. Lead 12 may seat loosely in device 10 or may "snap" into or otherwise be removably secured within device 10. Posterior convex surface 16 is adapted to contact the human's body tissue opposite electrical stimulation lead 12 (i.e. proximate the ligamentum flavum in the case of electrical stimulation of spinal nerve tissue). In one embodiment, the interior of device 10 between anterior concave surface 14 and posterior convex surface 16 is solid rather than hollow, although device 10 may be formed with a hollow interior if appropriate.

As shown in FIG. 1C, a leading end 20 of device 10 may extend beyond and at least partially surround a corresponding leading end 22 of lead 12 such that, when lead 12 is pushed in the direction of leading ends 20 and 22, device 10 is simultaneously pushed in the same direction and to the same extent. This may allow device 10 to be inserted more easily in association with lead 12. Instead or in addition, leading end 20 of device 10 may be tapered to allow device 10 to be inserted more easily. A trailing end of device 10 may similarly extend beyond and at least partially surround a corresponding trailing end of lead 12 to allow device 10 to be withdrawn more easily in association with lead 12. Instead or in addition, the trailing end of device 10 may be tapered to allow device 10 to be withdrawn more easily.

In one embodiment, upon insertion of device 10 into a region of a human's body such as the human's epidural space, device 10 may function as an anterior-posterior or other stabilizer for electrical stimulation lead 12 such that electrical stimulation lead 12 is not able to freely float within the human's epidural space. Stabilization of electrical stimulation lead 12 in the human's epidural space or other region of the body may be difficult without device 10 because it may be difficult to suture or otherwise fixate electrical stimulation lead 12 in position. Stabilization of electrical stimulation lead 12 in the human's epidural space or other region of the body may help improve performance, comfort, and overall treatment results.

Device 10 may be sized and shaped according to the type of target nerve tissue to be stimulated, the amount or type of electrical energy to be emitted from electrical stimulation lead 12, the space available within the human's body for electrical stimulation lead 12 and associated device 10, or any other suitable factors. In one embodiment, device 10 may be formed from material that is collapsible for easier removal from the human's epidural space or other region of the body. Instead or in addition, device 10 may be formed from material that is expandable such that it more completely fills the remaining epidural space or other region upon insertion and acts to buttress electrical stimulation lead 12 against the human's surrounding tissue for increased stability. Device 10 may be formed from material that is pliable enough to configure to the curvature of the human's epidural space or other region or to conform to any other suitable anatomical size or shape as necessary for insertion into the human's body. In one embodiment, for example, device 10 may be formed of polyurethane.

Figure 2A:
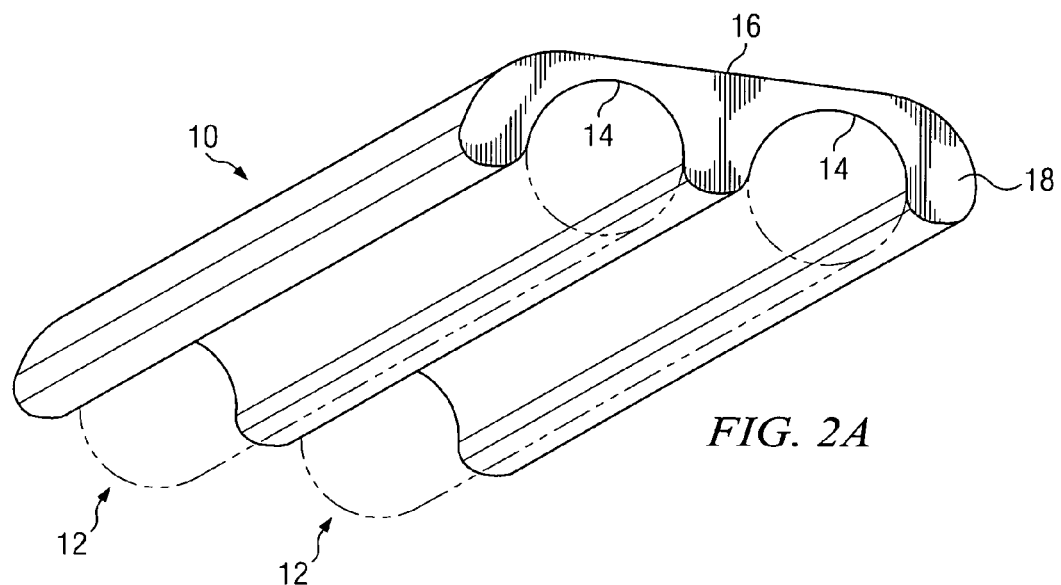
FIGS. 2A-2C illustrate views of another example device for partially shielding electrical energy emitted from multiple electrical stimulation leads implanted in a human's body, the device positioned proximate the electrical stimulation leads.
Figure 2B:
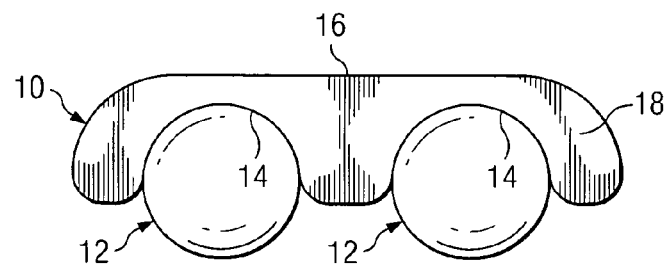
Figure 2C:
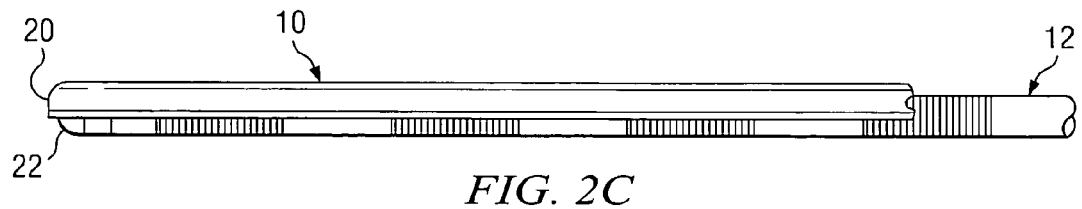

As shown in FIGS. 2A-2C, in other embodiments, device 10 may be configured to accommodate and shield electrical energy emitted from multiple electrical stimulation leads 12 according to particular needs. Although an example device 10 accommodating two leads 12 is shown, device 10 may be configured to accommodate any suitable number of leads 12 and the present invention is intended to encompass all such configurations. Device 10 may include one or more lobes 24 to separate adjacent leads 12. Lobe 24 may help position and stabilize leads 12 and may further shield electrical energy emitted from leads 12.

Figure 3:
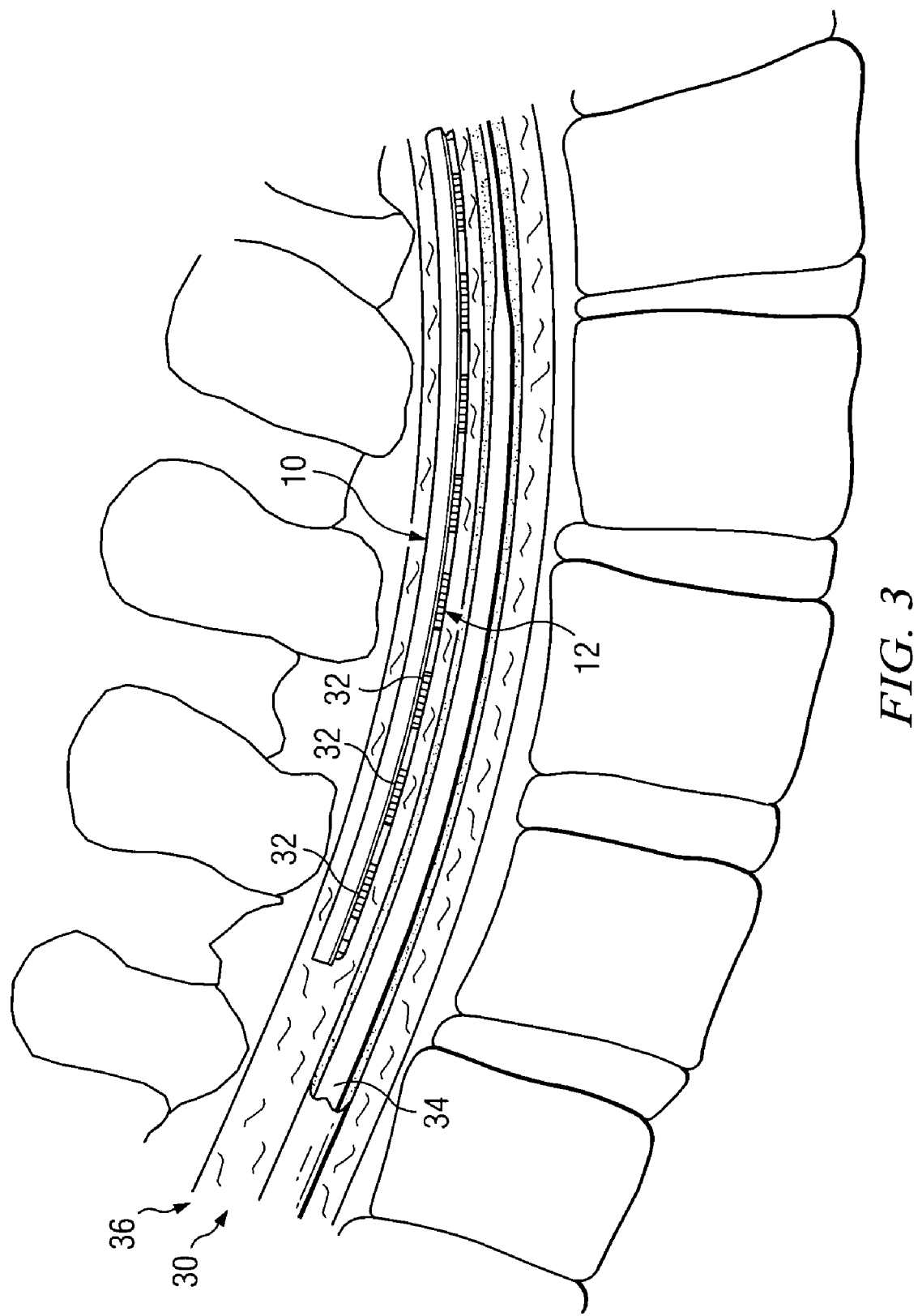
FIG. 3 illustrates an example of a device for partially shielding electrical energy emitted from an electrical stimulation lead, the device implanted proximate the electrical stimulation lead in a human's epidural space.

FIG. 3 illustrates an example of device 10 implanted proximate electrical stimulation lead 12 in a human's epidural space 30. In this example, electrodes 32 are circumferential electrodes located along the longitudinal axis of a percutaneous electrical stimulation lead 12 that emit electrical energy radially in all directions. Spinal cord 34 and ligamentum flavum 36 are also shown. Anterior concave surface 14 of device 10 partially surrounds a posterior side of electrical stimulation lead 12. Electrical stimulation lead 12 is positioned between anterior concave surface 14 of device 10 and spinal cord 34. Posterior convex surface 16 of device 10 is adapted to contact the human's body tissue proximate ligamentum flavum 36. Device 10 functions as an electrical energy shield between electrical stimulation lead 12 and ligamentum flavum 36 and associated tissue. Device 10 may also function as a spacer to position electrical stimulation lead 12 within epidural space 30 closer to spinal cord 34 and to help secure electrical stimulation lead 12 in position.

Now referring to FIGS. 4A-4B, there are shown two embodiments of an electrical stimulation system 200, 300 in accordance with the present invention. Stimulation system 200, 300 generates and applies a stimulus to a human's nerve tissue or to certain locations of the human's body. In general terms, stimulation system 200, 300 includes a stimulation or energy source 210, 310 and an electrical stimulation lead 110 for application of the stimulus. Lead 110 shown in FIGS. 4A-4B is lead 12 described above.

As shown in FIG. 4A, stimulation system 200 includes lead 110 coupled to stimulation source 210. In one embodiment, stimulation source 210 includes an implantable pulse generator (IPG). As is known in the art, an IPG is implanted within the human's body that is to receive electrical stimulation from stimulation source 210. An example IPG may be one manufactured by Advanced Neuromodulation Systems, Inc., such as the Genesis® System, part numbers 3604, 3608, 3609, and 3644.

As shown in FIG. 4B, stimulation system 300 includes lead 110 coupled to stimulation source 310. Stimulation source 310 includes a wireless receiver. As is known in the art, stimulation source 310 comprising a wireless receiver is implanted within the human's body that is to receive electrical stimulation from stimulation source 310. An example wireless receiver 310 may be those wireless receivers manufactured by Advanced Neuromodulation Systems, Inc., such as the Renew® System, part numbers 3408 and 3416.

The wireless receiver within stimulation source 310 is capable of receiving wireless signals from wireless transmitter 320. The wireless signals are represented in FIG. 4B by wireless link symbol 330. Wireless transmitter 320 and controller 340 are located outside of the human's body that is to receive electrical stimulation from stimulation source 310. A user of stimulation source 310 may use controller 340 to provide control signals for operation of stimulation source 310. Controller 340 provides control signals to wireless transmitter 320, wireless transmitter 320 transmits the control signals and power to a receiver in stimulation source 310, and stimulation source 310 uses the control signals to vary the signal parameters of the electrical signals that are transmitted through lead 110 to the stimulation site. An example wireless transmitter 320 may be those transmitters manufactured by Advanced Neuromodulation Systems, Inc., such as the Renew® System, part numbers 3508 and 3516.

As will be appreciated, the connectors are not visible in FIGS. 4A-4B because the contact electrodes are situated within a receptacle of stimulation source 210, 310. The connectors are in electrical contact with a generator of electrical signals within stimulation source 210, 310. Stimulation source 210, 310 generates and sends electrical signals via lead 110 to electrodes 160. Understandably, electrodes 160 are located at a stimulation site within the human's body that is to receive electrical stimulation from the electrical signals. A stimulation site may be, for example, adjacent one or more nerves in the central nervous system (e.g., spinal cord) or one or more peripheral nerves. Stimulation source 210, 310 is capable of controlling the electrical signals by varying signal parameters (e.g., intensity, duration, frequency) in response to control signals that are provided to stimulation source 210, 310.

Figure 5B:
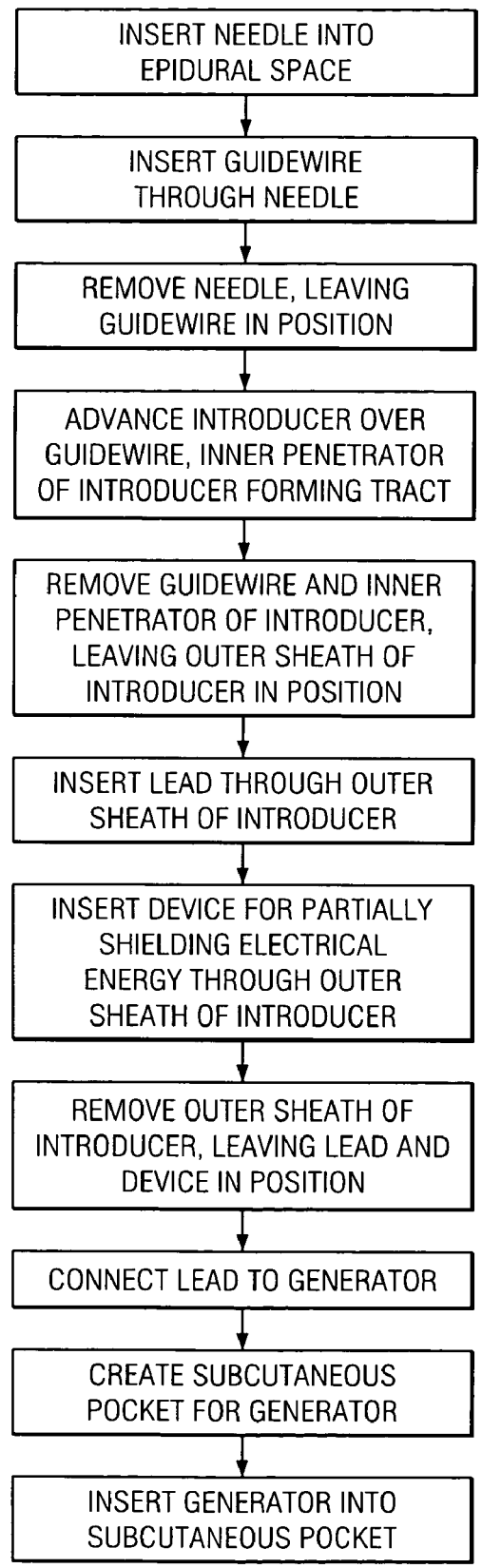

In one embodiment, lead 110 and associated device 10 are inserted into epidural space 20 or near a peripheral nerve using a suitable introducer. For example, lead 110 and associated device 10 may be inserted percutaneously using a needle according to standard techniques, as described more fully in FIG. 5A. As another example, lead 110 and associated device 10 may be inserted using an introducer having a hollow inner penetrator removably housed in a hollow outer sheath, as described more fully in FIG. 5B. Once lead 110 and device 10 have been inserted, lead 110 extends from the insertion site to the implant site. The implant site is typically a subcutaneous pocket that receives and houses the IPG or receiver (providing stimulation source 210, 310). The implant site is usually positioned a distance away from the stimulation site, such as near the buttocks or another place in the torso area. In many cases, the implant site and insertion site are located in the lower back area and lead 110 extends through epidural space 20 to the stimulation site (e.g., middle or upper back, neck, or brain areas). Once system 200, 300 is implanted, the system of leads and/or extensions may be subject to mechanical forces and movement in response to body movement. FIGS. 5A-5B illustrate example steps that may be used to implant an example stimulation system 200, 300 into a human for electrical stimulation of the human's spinal nerve tissue.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method of implanting first and second stimulation leads within the epidural space of a patient, comprising:
   providing first and second percutaneous stimulation leads that each comprise a plurality of electrodes;
   securing the first and second percutaneous stimulation leads within a device, the device being formed of a compressible material, and the device comprising:
   (i) a first anterior concave surface adapted to contact and at least partially surround a posterior side of the first electrical stimulation lead;
   (ii) a second anterior concave surface adapted to contact and at least partially surround a posterior side of the second electrical stimulation lead;
   (iii) a posterior convex surface coupled to the first and second anterior concave surfaces; and
   (iv) a lobe separating the first electrical stimulation lead and the second electrical stimulation lead;
   the securing occurring by snapping the first and second percutaneous leads into the first and second anterior concave surfaces respectively;
   inserting the device, with the first and second percutaneous leads secured thereto, through a needle into the epidural space of the patient, the device being compressed while proceeding through the needle, the device expanding upon entry into the epidural space of the patient to stabilize the first and second percutaneous stimulation leads in a side-by-side longitudinal arrangement within the epidural space of the patient;
   electrically coupling the first and second stimulation leads to an implantable pulse generator (IPG); and
   delivering stimulation pulses from the IPG to stimulate neural tissue of the patient using the first and second stimulation leads, wherein the first and second convex surfaces of the device partially shield electrical energy from the first and second stimulation leads.

2. The method of claim 1 wherein the device comprises a hollow interior.

3. The method of claim 2 wherein the hollow interior collapses when the device is inserted through the needle.

4. The method of claim 1 wherein the device comprises a solid interior.

5. The method of claim 1 wherein the device is formed of a polyurethane material.

6. The method of claim 1 wherein the device comprises a tapered trailing end for facilitating removal of the device, with the stimulation leads secured thereto, from the epidural space of the patient.

* * * * *